United States Patent [19]

Bair

[11] Patent Number: 4,855,453

[45] Date of Patent: Aug. 8, 1989

[54] TETRACYCLIC THIOPHENE DERIVATIVES

[75] Inventor: Kenneth W. Bair, Chapel Hill, N.C.

[73] Assignee: Burroughs Wellcome Co., Research Triangle Park, N.C.

[21] Appl. No.: 196,830

[22] Filed: May 16, 1988

Related U.S. Application Data

[63] Continuation of Ser. No. 801,087, Nov. 22, 1985, abandoned, which is a continuation-in-part of Ser. No. 673,356, Nov. 20, 1984, abandoned.

[51] Int. Cl.$^4$ .............................................. C07D 333/74
[52] U.S. Cl. ...................................... 549/42; 514/908
[58] Field of Search ........................................... 549/42

[56] References Cited

U.S. PATENT DOCUMENTS

| | | | |
|---|---|---|---|
| 2,894,003 | 7/1959 | Long | 549/457 |
| 3,514,458 | 5/1970 | Fields | 549/457 |
| 4,219,657 | 8/1980 | Berger et al. | 549/43 |

Primary Examiner—Robert W. Ramsuer
Attorney, Agent, or Firm—Donald Brown

[57] ABSTRACT

The present invention relates to anti tumor compounds of formula (I)

$$ArCH_2R^1 \qquad (I)$$

or a monomethyl or monoethyl ether thereof (the compound of formula (I) including these ethers may contain no more than 29 carbon atoms in total); ethers, esters thereof; acid addition salts thereof; wherein Ar is a fused tetracyclic aromatic ring system comprised of 5-membered and 6-membered rings and contains at least one heteroatom and 3 aromatic rings and a total of no more than 18 ring atoms, or a substituted derivative thereof; the heteroatom is preferably oxygen, sulfur or nitrogen; when it is nitrogen this is substituted by hydrogen, methyl or ethyl;

$R^1$ contains not more than eight carbon atoms and is a group

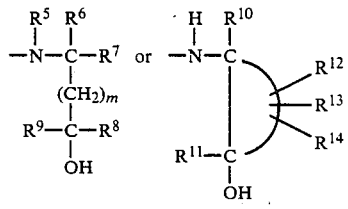

wherein
m is 0 or 1;
$R^5$ is hydrogen;
$R^6$ and $R^7$ are the same or different and each is hydrogen or $C_{1-5}$ alkyl optionally substituted by hydroxy;
$R^8$ and $R^9$ are the same or different and each is hydrogen or $C_{1-3}$ alkyl;

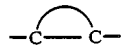

is a five or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl.

7 Claims, No Drawings

TETRACYCLIC THIOPHENE DERIVATIVES

This application is a continuation of application Ser. No. 801,087 filed Nov. 22, 1985, now abandoned, which is a continuation-in-part of application Ser. No. 673,356 filed Nov. 20, 1984, now abandoned.

The present invention relates to heteropolycyclic aromatic alkanol derivatives which have been found to have biocidal activity. More specifically the invention concerns aminoalkanol derivatives containing a heteropolycyclic aromatic ring system, methods for the synthesis thereof, novel intermediates therefor, pharmaceutical formulations thereof and the use thereof as antitumor agents.

Accordingly, in a first aspect, the present invention provides a compound of the formula (I)

$$ArCH_2R^1 \qquad (I)$$

or a monomethyl or monoethyl ether thereof (the compound of formula (I) including these ethers may contain no more than 29 carbon atoms in total); ethers, esters thereof; acid addition salts thereof; wherein Ar is a fused tetracyclic aromatic ring system comprised of 5-membered and 6-membered rings and contains at least one heteroatom and 3 aromatic rings and a total of no more than 18 ring atoms, or a substituted derivative thereof; the heteroatom is preferably oxygen, sulfur or nitrogen; when it is nitrogen this is substituted by hydrogen, methyl or ethyl; the ring/system is optionally substituted by one or two substituents; preferably the ring system is unsubstituted or mono-substituted (the substituents will contain not more than four carbon atoms in total when taken together being the same or different and are selected from halogen; cyano; $C_{1-4}$ alkyl or $C_{1-4}$ alkoxy, each optionally substituted by hydroxy or $C_{1-2}$ alkoxy; halogen substituted $C_{1-2}$ alkyl or $C_{1-2}$ alkoxy; a group $S(O)_nR^2$ wherein n is an integer 0, 1 or 2 and $R^2$ is $C_{1-2}$ alkyl optionally substituted by hydroxy or $C_{1-2}$ alkoxy; or the ring system is optionally substituted by a group $NR^3R^4$ containing not more than 5 carbon atoms wherein $R^3$ and $R^4$ are the same or different and each is a $C_{1-3}$ alkyl group or $NR^3R^4$ forms a five-or six-membered heterocyclic ring optionally containing one or two additional heteroatoms);

$R^1$ contains not more than eight carbon atoms and is a group

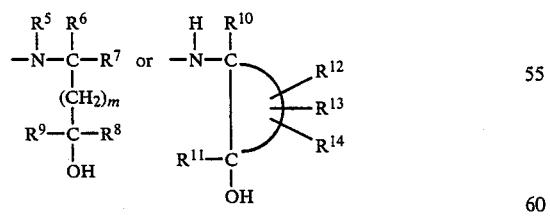

wherein
m is 0 or 1;
$R^5$ is hydrogen;
$R^6$ and $R^7$ are the same or different and each is hydrogen or $C_{1-5}$ alkyl optionally substituted by hydroxy;
$R^8$ and $R^9$ are the same or different and each is hydrogen or $C_{1-3}$ alkyl;

is a five- or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl.

Specific ring systems included within the scope of the present invention include;

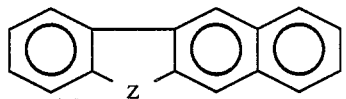

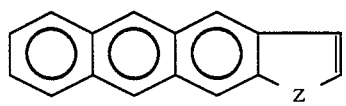

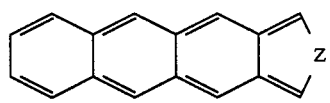

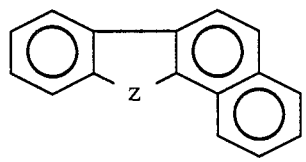

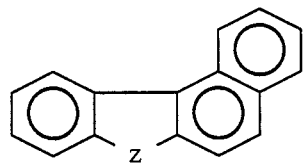

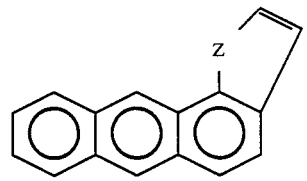

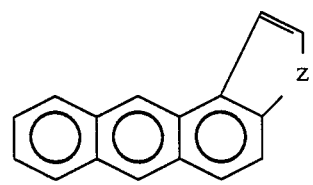

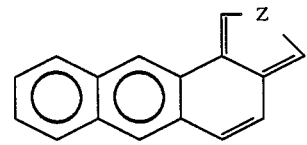

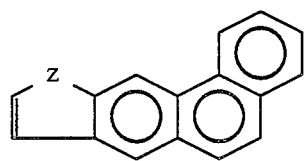
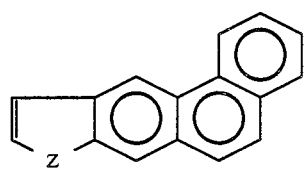
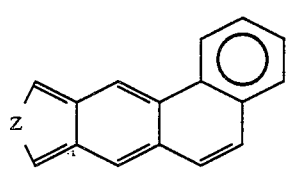
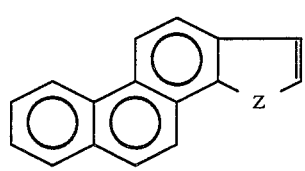
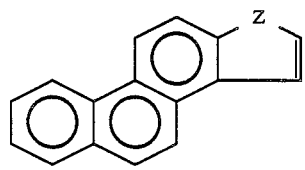
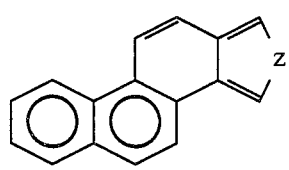
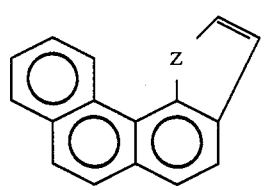
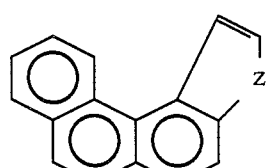
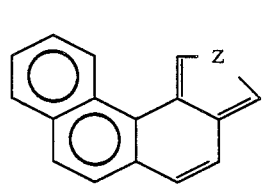
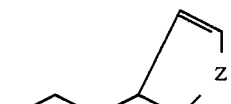
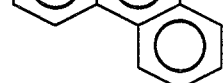
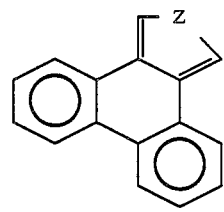
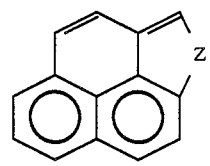
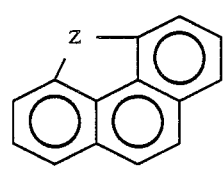
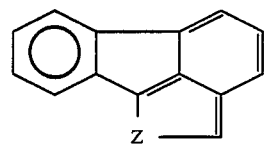
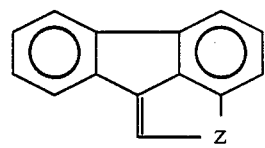
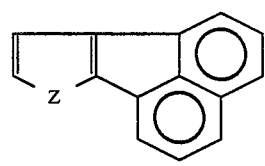
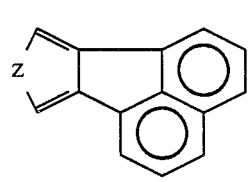

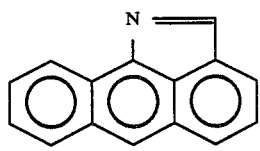
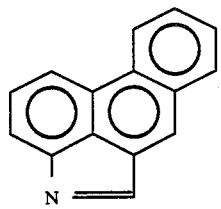
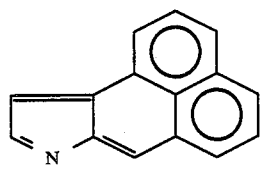
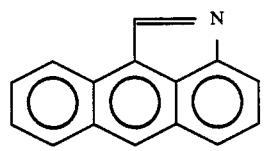
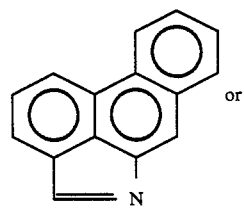 or
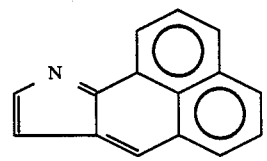
wherein Z is a heteroatom.
Suitably ArCH$_2$R$^1$ or a monomethyl or monethyl ether thereof contains not more than 28 carbon atoms in total.
Suitably Ar is
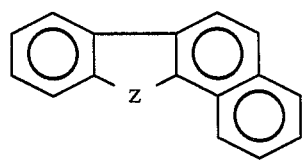
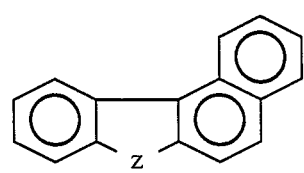
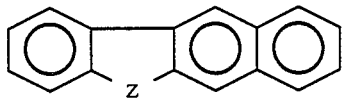
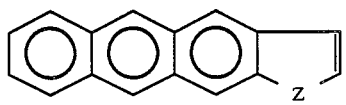
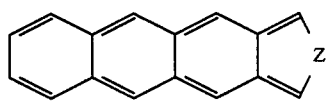
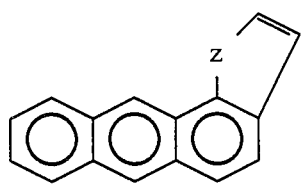
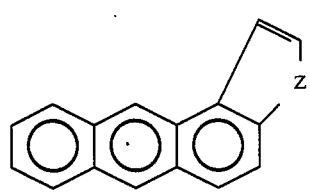
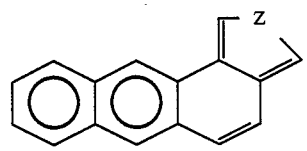
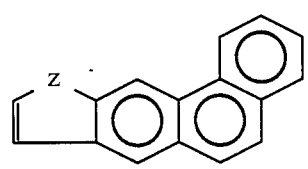
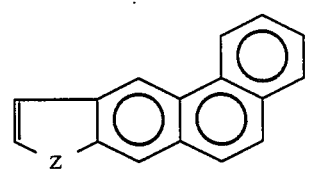
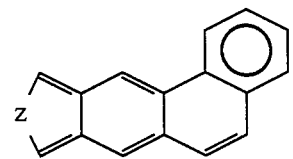
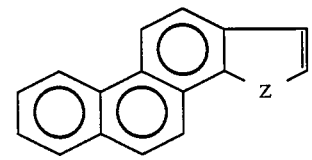

-continued
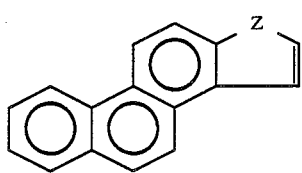
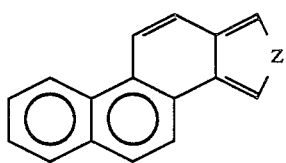
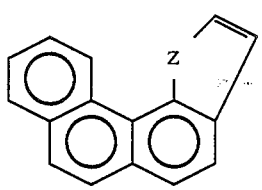
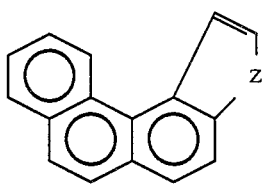
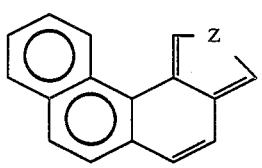
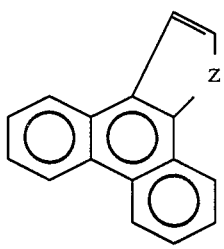
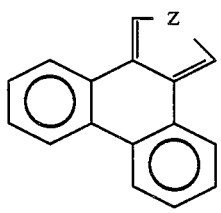
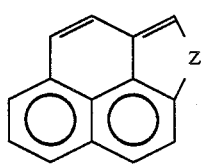
-continued
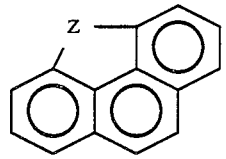
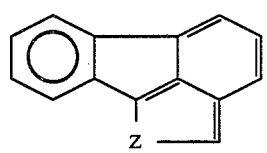
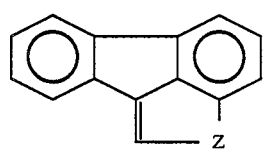
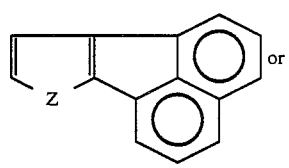
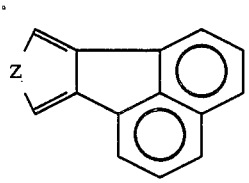
wherein Z is O, S, NH, NCH$_3$, or NEt.
More suitably Ar is
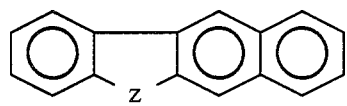
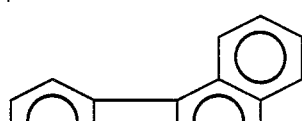
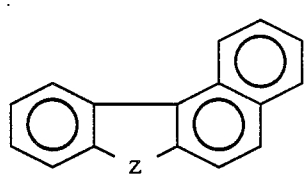
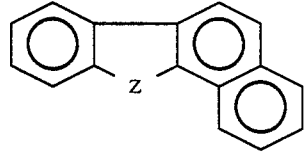
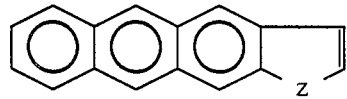

-continued
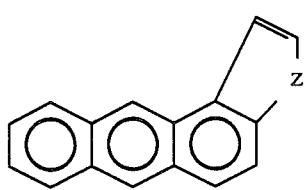
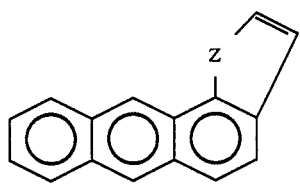
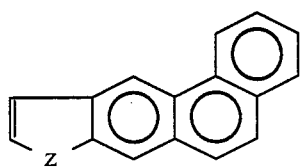
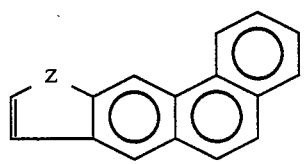
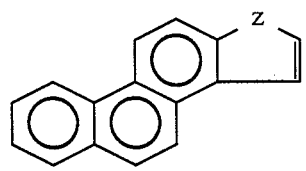
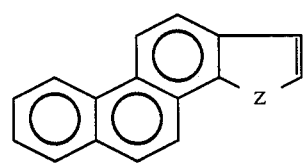
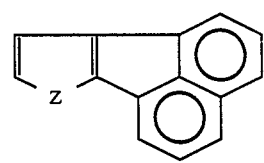
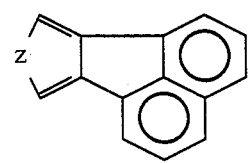
-continued
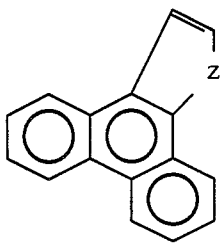
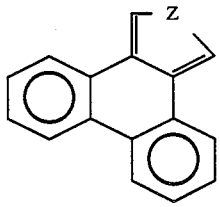
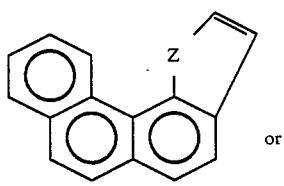
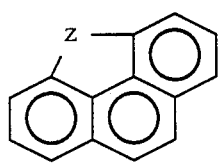
or
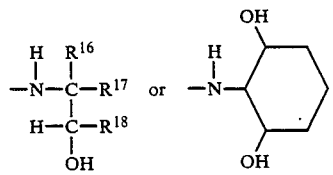
wherein Z=O, S, NH, $NCH_3$ or NEt; suitably $R^1$ is
$$-\overset{H}{\underset{H-\overset{|}{C}-R^{18}}{\underset{OH}{N}}}-\overset{R^{16}}{\underset{|}{C}}-R^{17} \quad \text{or} \quad -\overset{H}{N}-\text{(cyclohexane with two OH groups)}$$
wherein
$R^{16}$ is $CH_2OH$, $CH(CH_3)OH$ or $CH_2CH_2OH$,
$R^{17}$ is hydrogen, $C_{1-3}$ alkyl or $CH_2OH$,
$R^{18}$ is hydrogen or methyl.
Preferably Ar is

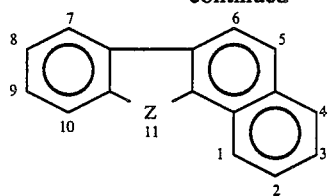

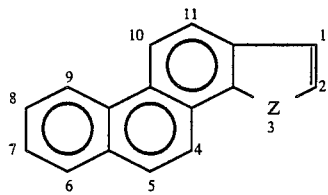

wherein Z=O, S, NH, NCH₃, NEt.
Most preferably Ar is

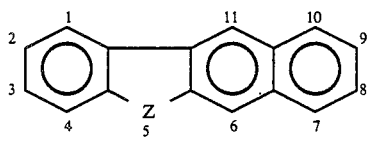

{ Z = O, Benzo[b]naphtho[2,3-d]furan-6-yl-,
  Z = O, Benzo[b]naphtho[2,3-d]furan-7-yl-,
  Z = O, Benzo[b]naphtho[2,3-d]furan-11-yl-,
  Z = S, Benzo[b]naphtho[2,3-d]thiophen-6-yl-,
  Z = S, Benzo[b]]naphtho[2,3-d]thiophen-7-yl-,
  Z = S, Benzo[b]naphtho[2,3-d]thiophen-8-yl-,
  Z = NR, 5-Ethyl-5H—benzo[b]carbazol-6-yl-,
  Z = NR, 5-Ethyl-5H—benzo[b]carbazol-7-yl-,

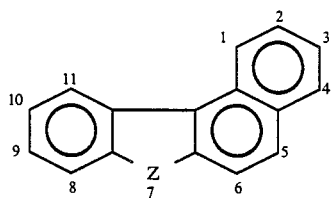

{ Z = O, Benzo[b]naphtho[1,2-d]furan-5-yl-,
  Z = S, Benzo[b]naphtho[1,2-d]thiophen-5-yl-,
  Z = NR, 7-Methyl-7H—benzo[c]carbazol-10-yl-,

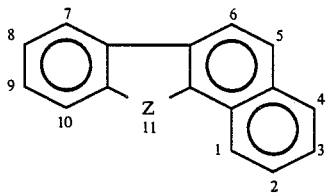

{ Z = O, Benzo[b]naphtho[2,1-d]furan-5-yl-,
  Z = S, Benzo[b]naphtho[2,1-d]thiophen-5-yl-,

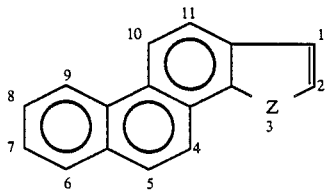

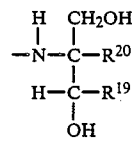

{ Z = O, Phenanthro[1,2-b]furan-11-yl- or
  Z = S, Phenanthro[1,2-b]thiophen-11-yl-;

preferably R¹⁶ is CH₂OH or CH(CH₃)OH; R¹⁷ is hydrogen, methyl, ethyl or CH₂OH.

Most preferably R¹ is a diol of the structure $$\begin{array}{c} H \quad CH_2OH \\ | \quad | \\ -N-C-R^{20} \\ | \\ H-C-R^{19} \\ | \\ OH \end{array}$$

wherein R¹⁹ is hydrogen or methyl and R²⁰ is hydrogen, methyl or ethyl, preferably methyl.

Acid addition salts included within the scope of the present invention are those of compound of formula (I) and ethers and esters thereof.

Esters and nonpharmaceutically useful salts of the compounds of the formula (I) are useful intermediates in the preparation and purification of compounds of the formula (I) and pharmaceutically useful acid addition salts thereof, and are therefore within the scope of the present invention. Thus, acid addition salts of the compounds of the formula (I) useful in the present invention include but are not limited to those derived from inorganic acids, such as hydrochloric, hydrobromic, sulfuric and phosphoric acids, organic acids such as isethionic (2-hydroxyethylsulfonic), maleic, malonic, succinic, salicylic, tartaric, lactic, citric, formic, lactobionic, pantothenic, methanesulfonic, ethanesulfonic, benzenesulfonic, p-toluenesulfonic, naphthalene-2-sulfonic, and ascorbic acids, and amino acids such as glycine.

Acid addition salts particularly useful as biocidal agents are those that are pharmacologically and pharmaceutically acceptable. Thus, suitable acid addition salts include but are not limited to those derived from hydrochloric, methanesulfonic, ethanesulfonic, isethionic, lactic, and citric acids.

The preferred pharmacologically and pharmaceutically acceptable salts are those that are soluble in solvents suitable for parenteral administration, for example, hydrochlorides, methanesulfonates and isethionates.

Esters of compounds of formula (I) are derived from acids known to those skilled in the art to be suitable for ester formation, and are conveniently those derived from C₁₋₆ alkanoic acids or alkanoic acid derivatives, for example acetic acid, propionic acid, n-butyric acid and iso-butyric acid. The esters may be formed from all or only some of the hydroxy groups contained in the compounds of formula (I). Specific compounds within the scope of formula (I) include;

2-[(Benzo[b]naphtho[2,1-d]thiophen-5-ylmethyl)amino]-2-methyl-1,3-propanediol,
2-[(Benzo[b]naphtho[2,3-d]furan-6-ylmethyl)amino]-2-methyl-1,3-propanediol,
2-[(Benzo[b]naphtho[1,2-d]furan-5-ylmethyl)amino]-2-methyl-1,3-propanediol,
2-Methyl-2-[[(7-methyl-7H-benzo[c]carbazol-10-yl)methyl]amino]-1,3-propanediol,
2-[(Benzo[b]naphtho[2,1-d]furan-5-ylmethyl)amino]-2-methyl-1,3-propanediol, 2-Methyl-2-[(phenanthro[1,2-b]furan-11-ylmethyl-
)amino]-1,3-propanediol,
2-Methyl-2-[(phenanthro[1,2-b]thiophen-2-ylmethyl-
)amino]-1,3-propanediol,
2-Methyl-2-[(phenanthro[1,2-b]thiophen-11-ylmethyl-
)amino]-1,3-propanediol,
2-Methyl-2-[(phenanthro[4,3-b]furan-2-ylmethyl-
)amino]-1,3-propanediol,
2-Methyl-2-[(phenanthro[4,3-b]thiophen-7-ylmethyl-
)amino]-1,3-propanediol,
2-Methyl-2-[(phenanthro[9,10-b]furan-2-ylmethyl-
)amino]1,3-propanediol,
2-Methyl-2[(phenanthro[9,10-c]thiophen-1-ylmethyl-
)amino]-1,3-propanediol, 2-[Acenaphtho-[1,2-b]thiophen-8-ylmethyl)amino]-2-methyl-1,3-propanediol,
2-[Acenaptho-[1,2-c]thiophen-7-ylmethyl)amino]-2-
methyl-1,3-propanediol,
2[(Benzo[b]naphtho[2,3-d]furan-7-ylmethyl)amino]-2-
methyl-1,3-propanediol,
2-[(Benzo[b]naphtho[2,3-d]thiophen-6-ylmethyl-
)amino]-2-methyl-1,3-propanediol,
2-[(Benzo[b]naphtho[2,3-d]thiophen-8-yl-methyl-
)amino]-2-methyl-1,3-propanediol,
2-[(Benzo[b]naphtho[2,3-d]thiophen-7-ylmethyl-
)amino]-2-methyl-1,3-propanediol,
2-[(Benzo[b]naphtho[2,3-d]furan-11-ylmethyl)amino]-2-
methyl-1,3-propanediol,
2-[(5-Ethyl-5H-benzo[b]carbazol-7-yl)methyl]amino]-2-
methyl-1,3-propanediol,
2-[[(5-Ethyl-5H-benzo[b]carbazol-6-yl)methyl]amino]-
2-methyl-1,3-propanediol,
2-[(Benzo[b]naphtho[1,2-d]thiophen-5-ylmethyl-
)amino]-2-methyl-1,3-propanediol and
2-Methyl-2-[(phenanthro[1,2-b]furan-2-ylmethyl-
)amino]1,3-propanediol;
ethers, esters thereof; acid addition salts thereof.

Of these specific examples of compounds of formula (I), the most preferred compounds of 2-methyl-2-[[(7-methyl-7H-benzo[c]carbazol-10-yl)methyl]amino]-1,3-propanediol and 2-[(benzo[b]naphtho[2,1-d]furan-5-ylmethyl)amino]-2-methyl-1,3-propanediol; ethers, esters thereof; acid addition salts thereof.

The compounds of formula (I) and their ethers, esters and salts thereof may be prepared by any method known in the art for the preparation of compounds of analogous structure. Thus, the compounds of formula (I) may, for example, be prepared by any of the methods defined below.

1. The reduction of a compound of formula (II)

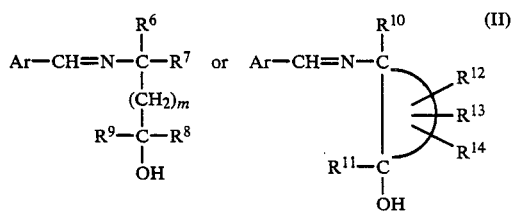

Wherein $R^2$–$R^4$ and $R^6$–$R^{14}$ are as hereinbefore defined or a suitably protected derivative thereof followed by deprotection where appropriate.

The conditions and reagents for such a reaction are well known to those skilled in the art, and any such conditions/reagents may be employed. The conversion of (II) or suitably protected derivatives thereof may be carried out by a reducing agent followed by deprotection if necessary. The reduction is conveniently carried out by a metal hydride such as lithium aluminum hydride, sodium borohydride, sodium cyanoborohydride, or by catalytic hydrogenation, conveniently by hydrogen in the presence of a metal catalyst such as palladium or platinum, or equivalent reagents as outlined by J. March, Advanced Organic Chemistry, 2nd ed., pages 819-820, McGraw Hill, New York, 1977. The reduction is suitably carried out with the compound of formula (II) in solution in an inert solvent or mixture of solvents compatible with the reducing agent, at a non-extreme temperature, for example, between 0° and 80° C., conveniently at room temperature.

In the case of lithium aluminum hydride and like reagents, suitable solvents include ethers (for example tetrahydrofuran, diethyl ether and 1,2-dimethoxyethane) optionally in the presence of a hydrocarbon cosolvent (for example toluene, benzene or hexane).

In the case of sodium borohydride and like reagents, suitable solvents include alcohols (for example ethanol, methanol or isopropanol) optionally in the presence of a hydrocarbon cosolvent (for example toluene, benzene or hexane) or an ether cosolvent (for example diethyl ether or tetrahydrofuran).

In the case of sodium cyanoborohydride and like reagents, suitable solvents include those described for sodium borohydride and in the presence of an acid conveniently glacial acetic acid or ethanolic hydrochloric acid as outlined in, for example, R. Hutchins et. al., Organic Preparations and Procedures International 11, 201 (1979).

In the case of catalytic hydrogenation, suitable solvents include alcohols (for example methanol and ethanol) optionally in the presence of a hydrocarbon cosolvent (for example toluene or benzene) or ether cosolvent (for example diethyl or tetrahydrofuran) in the presence of an acid (for example glacial acetic acid or ethanolic hydrochloric acid) or in glacial acetic acid.

Protected derivatives of compounds of formula (II) are conveniently used when lithium aluminum hydride is employed as the reducing agent. Convenient protecting groups are compatible with the reducing agent utilized and are readily removed under nondestructive conditions, for example benzyl, tetrahydropyranyl and isopropylidene ethers.

It is often convenient not to isolate the compound of the formula (II) but to react a compound of the formula (III) with a compound of the formula (IV):

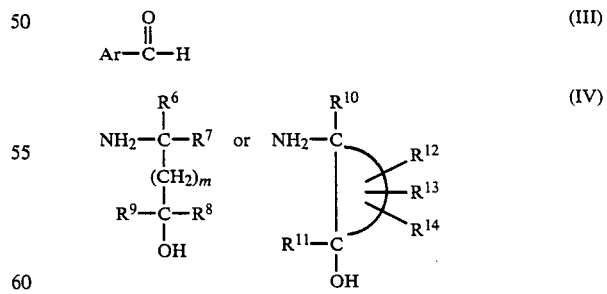

wherein Ar and $R^2$–$R^4$ and $R^6$–$R^{14}$ are as defined in (I), and reduce the compound of the formula (II) so formed in situ. The reaction of the compounds of the formulae (III) and (IV) is again suitably carried out using conditions and reagents which are well known to those skilled in the art, for example in the presence of an acid, such as a sulfonic acid, i.e., p-toluenesulfonic acid, in an appropriate inert solvent, such as an aromatic hydrocarbon, suitably toluene, with azeotropic removal of water followed by treatment with the reducing agent in an appropriate solvent, suitably ethanol or methanol. Alternatively, (II) formed under equilibrium conditions in appropriate solvents can be reduced in situ with an appropriate reducing agent, suitably sodium cyanoborohydride. The compound of formula (III) may be in the form of a protected aldehyde, for example an acetal, which liberates the aldehyde function under the reaction conditions.

In turn, a compound of formula (III) can be synthesized by reacting the appropriate aromatic heteropolycycle with a formylating agent such as that generated by the reaction between $SnCl_4$ and $Cl_2CHOCH_3$ or equivalent reagents, for example, according to the method of A. Rieche et al., Chem. Ber. 93, 88 (1960), or with other standard formylating reagents/procedures known to the art, for example, the Gatterman-Koch reaction ($CO/HCl/AlCl_3/CuCl$), the Gatterman reaction ($HCN/HCl/ZnCl_2$), and the Vilsmeier reaction ($POCl_3/PhN(Me)CHO$, or $POCl_3/Me_2NCHO$) (J. March, vide supra, pages 494–497).

The compounds of the formula (III) may also be prepared from an appropriate aromatic heteropolycycle substituted by a suitable functional group such as (but not limited to) esters, $CH_2OH$, $CHBr_2$, $CH_3$, $COCH_3$, $COOH$, or $CN$, and converting this functional group to an aldehyde group by methods well known to those skilled in the art.

Where the aromatic heteropolycycle bears substituents, the compound of formula (III) may be prepared by a variety of methods known in the art of organic chemistry depending on the nature of the substituent on the heteropolycyclic ring. For example, if the substituent(s) is a halogen, the starting materials may be prepared by direct treatment of the aromatic heteropolycycle with a halogenating agent (e.g., $Cl_2$, $Br_2$, or $SO_2Cl_2$) or indirectly by such routes as the Sandmeyer reaction (H. H. Hodgson, Chem. Rev. 40, 251 (1947). If the substituent(s) is alkyl, the aromatic heteropolycycle may be reacted with the appropriate reagents under Friedel-Crafts reaction conditions (G. A. Olah, *Friedel Crafts and Related Reactions*, Vols. 1–3, Interscience, New York, NY, 1963–1965).

In appropriate cases, the compounds of the formula (IV) and ethers thereof also may be prepared by methods known in the art, for example, by the reaction of a compound of the formula (V)

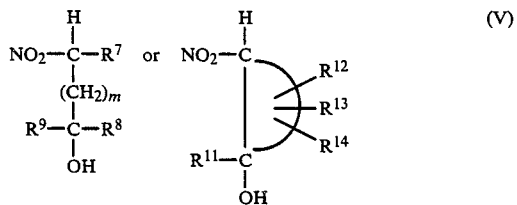

(or ethers thereof) wherein $R^7$–$R^9$ and $R^{11}$–$R^{14}$ and m are as hereinbefore defined with an appropriate aldehyde, conveniently acetaldehyde or formaldehyde (as in B. M. Vanderbilt and H. B. Hass, *Ind. Eng. Chem.* 32, 34 (1940)) followed by reduction (as outlined in J. March, vide supra, pages 1125–1126), conveniently by hydrogen and a metal catalyst (for example, a platinum containing catalyst) in an appropriate solvent, conveniently glacial acetic acid.

2. The reduction of a compound of the formula (VI)

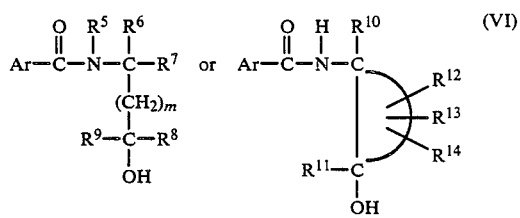

wherein Ar and $R^2$–$R^{14}$ are as hereinbefore defined and the hydroxy groups are optionally protected, followed by deprotection of the hydroxy groups where appropriate. The reduction may be carried out by standard reducing agents known for carrying out this type of reduction (as outlined in J. March, vide supra page 1122), for example, a hydride reagent such as lithium aluminum hydride in an inert solvent, such as an ether, i.e. tetrahydrofuran, at a non-extreme temperature, for example, at between 0° and 100° C. and conveniently at the reflux temperature of the ether. The compound of the formula (VI) may be formed by the reaction of the appropriate acid (ArCOOH) or a suitable reactive acid derivative thereof (as outlined in J. March, vide supra, pages 382–390), for example, an acid halide, in an inert solvent with an amine of the formula (IV) in which the hydroxy groups are optionally protected, for example, when the compound of the formula (IV) is a diol, by an isopropylidene group. The compound of the formula (VI) so formed is suitably reduced in situ and deprotected if necessary to give a compound of formula (I). The compounds of the formula ArCOOH can be prepared by methods well known to those skilled in the art.

3. The reaction of a compound $ArCH_2L$ (wherein Ar is as hereinbefore defined and L is a leaving group) with a compound of the formula (IV) as hereinbefore defined. Suitable leaving groups are those defined by J. March, vide supra, pages 325–331, and include halogens such as chlorine and bromine and sulfonic acid derivatives such as p-toluenesulfonate. The reaction is suitably carried out in an appropriate solvent, such as a dipolar aprotic solvent or alcohol at a non-extreme temperature, for example 50°–100° C. The compounds of the formula $ArCH_2L$ can be prepared by methods well known to those skilled in the art.

There is therefore provided, as a further aspect of the invention, a method for the preparation of a compound of formula (I) comprising any method known for the preparation of analogous compounds, in particular those methods defined in (1) to (3) hereinabove.

The compounds of this invention have are toxic to certain living cells which are detrimental to mammals, for example pathogenic organisms and tumor cells. While the compounds herein have activity, it should be appreciated that the range and level of activity may vary from compound to compound, and therefore the compounds are not necessarily equivalent.

This toxicity to pathogenic organisms has been demonstrated by activity against viruses (e.g., *Herpes simplex 1*/vero), fungi (e.g., *Candida albicans*), protozoa (e.g., *Eimeria tenella* and *Trichomonas vaginalis*), bacteria (e.g., *Mycoplasma smegmatis* and *Streptococcus* pyogenes), and helminths (e.g., *Nippostrongylus brasiliensis*). The antitumor activity of compounds of formula (I) has been demonstrated in a number of recognized screens and primarily by activity against ascitic P388/0 leukemia.

Preferred compounds of the formula (I) are those which have antitumor activity. The activity against ascitic tumors, including P388/0, is evidenced by reduction of tumor cell number in mammals (for example, mice bearing ascitic tumors) and consequent increase in survival duration as compared to an untreated tumor-bearing control group. Antitumor activity is further evidenced by measurable reduction in the size of solid tumors following treatment of mammals with the compounds of this invention compared to the tumors of untreated control tumor-bearing animals. Compounds of formula (I) are active against murine tumors such as lymphocytic leukemia P388/0, lymphocytic leukemia L1210, melanotic melanoma B16, P815 mastocytoma, MDAY/D2 fibrosarcoma, colon 38 adenocarcinoma, M5076 rhabdomyosarcoma and Lewis lung carcinoma.

Activity in one or more of these tumor tests has been reported to be indicative of antitumor activity in man (A. Goldin et al., in *Methods in Cancer Research* ed. V. T. DeVita Jr. and H. Busch, 16 165, Academic Press, N.Y. 1979).

There are sublines of P388/0 which have been made resistant to the following clinically useful agents: cytosine arabinoside, doxorubicin, cyclophosphamide, L-phenylalanine mustard, methotrexate, 5-fluorouracil, actinomycin D, cis-platin and bis-chloroethylnitrosourea. Compounds of this invention show potent activity against these drug-resistant tumors using the procedure for P388/0 above.

Compounds of formula (I) have also been found to be active against human tumor cells in primary cultures of lung, ovary, breast, renal, melanoma, unknown primary, gastric, pancreatic, mesothelioma, myeloma, and colon cancer. As used herein "cancer" is to be taken as synonymous with "malignant tumor" or more generally "tumor" unless otherwise noted. This is a procedure in which the prevention of tumor cell colony formation, i.e., tumor cell replication, by a drug has been shown to correlate with clinical antitumor activity in man (D. D. Von Hoff et al., *Cancer Chemotherapy and Pharmacology* 6, 265 (1980); S. Salmon and D. D. Von Hoff, *Seminars in Oncology*, 8, 377 (1981)).

Compounds of formula I which have been found to have antitumor activity intercalate in vitro with DNA (this property is determined by viscometric methods using the procedure of W. D. Wilson et al., *Nucleic Acids Research* 4, 2697 (1954)) and a log P as calculated by the method of C. Hansch and A. Leo in *Substituent Constants for Correlation Analysis in Chemistry and Biology*, John Wiley and Sons, New York, 1979, lying in the range between −2.0 and +2.5.

As has been described above, the compounds of the present invention are useful for the treatment of animals (including humans) bearing susceptible tumors. The invention thus further provides a method for the treatment of tumors in animals, including mammals, especially humans, which comprises the administration of a clinically useful amount of compound of formula (I) in a pharmaceutically useful form, once or several times a day or other appropriate schedule, orally, rectally, parenterally, or applied topically.

In addition, there is provided as a further, or alternative, aspect of the invention, a compound of formula (I) for use in therapy, for example as an antitumor agent.

The amount of compound of formula (I) required to be effective as a therapeutic agent will, of course, vary and is ultimately at the discretion of the medical or veterinary practitioner. The factors to be considered include the condition being treated, the route of administration, the nature of the formulation, the mammal's body weight, surface area, age and general condition, and the particular compound to be administered. A suitable effective antitumor dose is in the range of about 0.1 to about 120 mg/kg body weight, preferably in the range of about 1.5 to 50 mg/kg, for example 10 to 30 mg/kg. The total daily dose may be given as a single dose, multiple doses, e.g., two to six times per day, or by intravenous infusion for a selected duration. For example, for a 75 kg mammal, the dose range would be about 8 to 9000 mg per day, and a typical dose would be about 2000 mg per day. If discrete multiple doses are indicated, treatment might typically be 500 mg of a compound of formula (I) given 4 times per day in a pharmaceutically useful formulation.

While it is possible for the active compound (defined herein as compound of formula (I), or ether, ester, or salt thereof) to be administered alone, it is preferable to present the active compound in a pharmaceutical formulation. Formulations of the present invention, for medical use, comprise an active compound together with one or more pharmaceutically acceptable carriers thereof and optionally other therapeutical ingredients. The carrier(s) must be pharmaceutically acceptable in the sense of being compatible with the other ingredients of the formulation and not deleterious to the recipient thereof.

The present invention, therefore, further provides a pharmaceutical formulation comprising a compound of formula (I) (in the form of the free base, ether, or ester derivative or a pharmaceutically acceptable acid addition salt thereof) together with a pharmaceutically acceptable carrier therefor.

There is also provided a method for the preparation of a pharmaceutical formulation comprising bringing into association a compound of formula (I), an ether, ester, or pharmaceutically acceptable salt thereof, and a pharmaceutically acceptable carrier therefor.

While the antitumor activity of the compounds of formula (I) is believed to reside in the free base, it is often convenient to administer an acid addition salt of a compound of formula (I).

The formulations include those suitable for oral, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into assocation with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent. Molded tablets may be made by molding in a suitable machine, a mixture of the powdered active compound with any suitable carrier.

A syrup may be made by adding the active compound to a concentrated, aqueous solution of a sugar, for example sucrose, to which may also be added any accessory ingredients. Such accessory ingredient(s) may include flavorings, an agent to retard crystallization of the sugar or an agent to increase the solubility of any other ingredient, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of the formula (I) that is isotonic with the blood of the recipient. Thus, such formulations may conveniently contain distilled water, 5% dextrose in distilled water or saline and a pharmaceutically and pharmacologically acceptable acid addition salt of a compound of the formula (I) that has an appropriate solubility in these solvents, for example the hydrochloride, isethionate and methanesulfonate salts, preferably the latter.

Useful formulations also comprise concentrated solutions or solids containing the compound of formula (I) which upon dilution with an appropriate solvent give a solution suitable for parental administration above.

In addition to the aforementioned ingredients, the formulations of this invention may further include one or more accessory ingredient(s) selected from diluents, buffers, flavoring agents, binders, surface active agents, thickeners, lubricants, preservatives (including antioxidants) and the like.

The following examples are provided by the way of illustration of the present invention and should in no way be construed as a limitation thereof.

General Comments

All solvents were reagent grade and used without further purification with the following exceptions. THF was dried by distillation from Na/K alloy under nitrogen ($N_2$) and used immediately. Toluene ($PhCH_3$) was distilled from $CaH_2$ under $N_2$ and stored over 3 Å molecular sieves. Chemicals used were reagent grade and used without purification unless noted. The full name and address of the suppliers of the reagents and chemicals is given when first cited. After this, an abbreviated name is used.

Preparative HPLC was carried out on a Water's Prep LC/System 500A machine using two 500 g silica gel ($SiO_2$) cartridges unless otherwise noted. Plugs of $SiO_2$ used for purifications were "flash chromatograph" $SiO_2$ (Merck & Co., Inc., Merck Chemical Division, Rahway, NJ 07065, Silica Gel 60, 230–400 mesh). In this procedure, an appropriate volume sintered glass funnel was filled approximately ¾ full with the $SiO_2$ and packed evenly by tapping the outside of the funnel. A piece of filter paper was then placed on top of the $SiO_2$ and a solution of the material to be purified applied evenly to the top. Gentle suction through a filter flask moved the eluting solvent through the plug rapidly. The appropriate size fractions were combined as needed and further manipulated.

General procedures are described in detail. Analogous procedures show melting point (mp), recrystallization solvents, and elemental analyses (all elements analyzing within a difference of $\leq 0.4\%$ of the expected value). Any changes to the procedure such as solvent, reaction temperature, reaction time, or workup are noted.

NMR ($^1H$, $^{13}C$), IR and MS data of all new products were consistent with the expected and proposed structures. The positions assigned to structural isomers were unequivocally determined by a number of NMR techniques. All final products were dried in a vacuum oven at 20 mm Hg pressure at the temperature indicated overnight (12–16 h). All temperatures are in degrees Celsius. Other abbreviations used are: room temperature (RT), absolute (abs.), round bottom flask (RB flask), minutes (min), hours (h).

EXAMPLE 1

2-[(Benzo[b]naphtho[2,1-d]thiophen-5-ylmethyl)amino]-2-methyl-1,3-propanediol methanesulfonate To a 3-necked RB flask equipped with magnetic stirring bar, condenser, thermometer, Dean-Stark trap, and $N_2$ inlet line with bubbler was added benzo[b]naphtho[2,1-d]thiophene-5-carbaldehyde (H. G. Pars Pharmaceutical Laboratories, Inc., 763 Concord Avenue, Cambridge, MA 02138, 4.94 g, 18.83 mmol), 2-amino-2-methyl-1,3-propanediol (Aldrich Chemical Co, P. O. Box 2060, Milwaukee, WI 53201, 1.98 g, 18.83 mmol), p-toluenesulfonic acid monohydrate (Aldrich, 0.1 g) and $PhCH_3$ (200 mL). The mixture was stirred at reflux with removal of $H_2O$ for 2.5 h (or until no $H_2O$ is collected). Most of the $PhCH_3$ was then removed by distillation. The mixture was then cooled in an ice bath and diluted with abs. EtOH (200 mL) and further cooled. Solid $NaBH_4$ (MCB Manufacturing Chemists, Inc., 2909 Highland Ave., Cincinnati, OH 45212, 0.712 g, 18.83 mmol) was added in one portion to the reaction mixture. The ice bath was then removed, the reaction mixture allowed to warm to RT and stirred overnight. The reaction was then acidified with 10% HCl and the solvents removed by rotary evaporation. The crude solid was shaken with 1N HCl (300 mL) filtered, washed with 1N HCl (300 mL), sucked semidry, and washed with $Et_2O$ (300 mL). The material was dissolved in $CH_3OH$ (200 mL), filtered and basified with 1N NaOH solution (1 L). A white solid formed which was extracted with EtOAc (3×500 mL). The EtOAc washings were combined, filtered, washed with saturated NaCl (3×500 mL), dried ($K_2CO_3$), filtered and concentrated by rotary evaporation to give a white solid. This was dissolved in a mixture of abs. EtOH (200 mL) and $CH_3SO_3H$ (99.5%, Morton Thiokol, Inc.—Alfa Products, P. O. Box 299, 152 Andover Street, Danvers, MA 01923, 3 mL), filtered and dilluted to 4 L with a mixture of $Et_2O$/hexane (1:1). This material was then recrystallized (EtOH/hexane, 1:3) to give 2-

[(benzo-[b]-naphthol[2,1-d]thiophen-5-ylmethyl-)amino]-2-methyl-1,3-propanediol methanesulfonate, mp 221°-222° (C,H,N,S).

Alternatively, the crude reaction mixture could be treated with 1N NaOH solution or H₂O before the solvents were removed. After thorough washing with H₂O and drying the resulting crude solid converted to its acid addition salt with either ethanolic HCl or methanesulfonic acid. Recrystallization of the resulting salt can be accomplished using i-PrOH, CH₃OH, EtOH or other alcohols alone or in combination with a nonpolar solvent such as Et₂O, hexane, PhCH₃ or other inert solvents.

EXAMPLE 2

2-[(Benzo[b]naphtho[2,3-d]furan-6-ylmethyl)amino]-2-methyl-1,3-propanediol

2A. Benzo[b]naphtho[2,3-d]furan-6-carbaldehyde
2B. Benzo[b]naphtho[2,3-d]furan-11-carbaldehyde Benzo[b]naphtho[2,3-d]furan (H. G. Pars Pharmaceutical Laboratories, Inc.) was formylated using the procedure of A. Rieche et al., *Chem. Ber.* 93, 88 (1960). The crude aldehyde appeared to be mainly one isomer accompanied by a small amount of a second aldehyde by TLC. Purification by chromatography (SiO₂, PhCH₃) followed by recyrstallization (CH₂Cl₂/hexane) gave the main component in 58% yield identified using NMR techniques to be benzo[b]naphtho[2,3-d]furan-6-carbaldehyde, (2A) mp 169°-171.5°, (C,H). The minor component, obtained in 3.4% yield was shown by NMR to be benzo[b]naphtho[2,3-d]-furan-11-carbaldehyde, mp 128°-132°, (C,H), (PhCH₃/hexane).

2B. 2-[(Benzo[b]naphtho[2,3-d]furan-6-ylmethyl]-2-methyl-1,3-propanediol methanesulfonate.0.4 H₂O Using the reductive amination procedure described in Example 1, benzo[b]naphtho[2,3-d]furan-6-carbaldehyde (2A) and 2-amino-2-methyl-1,3-propanediol (Aldrich) gave a 64.7% yield of 2-[(benzo[b]naphtho[2,3-d]furan-6-ylmethyl)amino-2-methyl-1,3-propanediol methanesulfonate. 0.4 H₂O, mp 187°-190°, (C,H,N,S), (EtOH/Et₂O).

EXAMPLE 3

2-[(Benzo[b]naphtho[1,2-d]furan-5-ylmethyl)amino]-2-methyl-1,3-propanediol

3A. Benzo[b]naphtho[1,2-d]furan-5-carbaldehyde

Benzo[b]naphtho[1,2-d]furan (H. G. Pars Pharmaceutical Laboratories, Inc.) was formylated using the procedure of A. Rieche et al., *Chem. Ber.* 93, 88 (1960). The crude aldehyde appeared to be only one isomer by TLC. Purification by chromatography (SiO₂, PhCH₃) followed by recrystallization (CH₂Cl₂/hexane) gave pure material (39% yield), identified using NMR techniques to be benzo[b]naphtho[1,2-d]-furan-5-carbaldehyde, mp 143°-145°, (C,H).

3B. 2-[(Benzo[b]naphtho[1,2-d]furan-5-ylmethyl)amino]-2-methyl-1,3-propanediol methanesulfonate Using the reductive amination procedure described in Example 1, benzo[b]naphth[1,2-d]furan-5-carbaldehyde (3A) and 2-amino-2-methyl-1,3-propanediol (Aldrich) gave a 72.1% yield of 2-[(benzo[b]naphtho[1,2-d]furan-5-ylmethyl)amino]-2-methyl-1,3-propanediol methanesulfonate, mp 215°-217°, (C,H,N,S), (EtOH/Et₂O).

EXAMPLE 4

2-Methyl-2-[[(7-methyl-7H-benzo[c]-carbazol-10-yl)methyl]amino]-1,3-propanediol 4A. 7-Methyl-7H-benzo[c]carbazole To a RB flask equipped with magnetic stirring bar, reflux condenser and N₂ inlet line with bubbler was added 7H-benzo[c]carbazole (H. G. Pars Pharmaceutical Laboratories, Inc., 6.6 g, 30.4 mmol) and dry THF (250 mL). To the flask was added in one portion potassium t-butoxide (Aldrich, 4.2 g, 37.4 mmol). Dimethylsulfate (Aldrich, 7.56 g, 60.0 mmol, 5.9 mL) was added dropwise to the solution and the mixture stirred for 15 min. TLC (SiO₂/PhCH₃) showed the reaction to be complete. The reaction mixture was then poured into a 1N NaOH solution (2L) and stirred. The white solid which formed was collected by filtration, washed with H₂O (3×500 mL), sucked semidry, dissolved in PhCH₃ (300 mL) and eluted through a plug of SiO₂ (5×5 cm) using PhCH₃ as the eluting solvent. Appropriate fractions were combined and the solvent removed to give a crude white product. This material was dissolved in CH₂Cl₂ (400 mL), filtered and diluted to 1 L with hexane. The mixture was concentrated to 500 mL by rotary evaporation. A white solid formed which was filtered, washed with pentane and dried in a vacuum to give 5.0 g of 7-methyl-7H-benzo[c]carbazole, mp 116°-118°, (C,H,N). A further 1.06 g of product was obtained on standing and further concentration of the filtrate to give a combined yield of 87.3%.

4B. 7-Methyl-7H-benzo[c]carbazole-10-carbaldehyde
4C. 7-Methyl-7H-benzo[c]carbazole-5-carbaldehyde 7-Methyl-7H-benzo[c]carbazole (4A) was formylated using the procedure of A. Rieche et al., *Chem. Ber.* 93, 88 (1960). TLC (SiO₂/PhCH₃) showed that the crude mixture contained two aldehydes. Column chromatography (SiO₂/PhCH₃) followed by crystallization (CH₂Cl₂/pentane) gave each of the aldehydes in isomerically pure form. A total of 3.83 g (59.1%) of the more mobile main component, 7-methyl-7H-benzo[c]carbazole-10-carbaldehyde, mp 164°-165°, (C,H,N). A total of 0.55 g (8% of a minor, less mobile component was identified by NMR as 7-methyl-7H-benzo[c]carbazole-5-carbaldehyde, mp 210°-213° (C,H,N).

4D. 2-Methyl-2-[[(7-methyl-7H-benzo[c]carbazol-10-yl)methyl]amino]-1,3-propanediol hydrochloride.0.3-H₂O Using the procedure outlined in Example 1, 7-methyl-7H-benzo[c]carbazole-10-carbaldehyde (4B) and 2-amino-2-methyl-1,3-propanediol (Aldrich) gave 2-methyl-2-[[(7-methyl-7H-benzo[c]carbazol-10-yl)methyl]amino]-1,3-propanediol hydrochloride 0.3H₂O, mp 229°-230° (dec), (C, H, N, Cl), (EtOH/Et₂O).

EXAMPLE 5

2-[((Benzo[b]naphtho[2,1-d]furan-5-ylmethyl)amino-2-methyl)-1,3-propanediol

5A. Benzo[b]naphtho[2,1-d]furan-5-carbaldehyde

Benzo[b]naphtho[2,1-d]furan (H. G. Pars Pharmaceutical Laboratories, Inc.) was formylated according to the procedure of A. Rieche et al., *Chem. Ber.* 93, 88 (1960). The crude product appeared to contain only one aldehyde. The crude material was then purified by flush chromatography on SiO₂ with CH₂Cl₂ as the eluting solvent. The appropriate fractions were combined and the solvent removed to give the crude material which was then recrystallized (CH₂Cl₂/hexane) to give a 78% yield of benzo[b]naphtho[2,1-d]furan-5-carbaldehyde, mp 123°-125°, (C, H).

5B. 2-[(Benzo[b]naphtho[2,1-d]furan-5-ylmethyl)amino]-2-methyl-1,3-propanediol methanesulfonate Using the procedure outlined in Example 1, benzo[b]naphtho(2,1-d]furan-5-carbaldehyde (5A) and 2-amino-2-methyl-1,3-propanediol (Aldrich) gave a 59.2% yield of 2-[(benzo[b]naphtho[2,1-b]furan-5-ylmethyl)amino]-2-methyl-1,3-propanediol methanesulfonate, mp 216°-218°, (C, H, N, S), EtOH/Et₂O).

EXAMPLE 6

2-[(Benzo[b]naphtho[2,3-d]furan-7-ylmethyl)amino]-2-methyl-1,3-propanediol 6A. 7-Bromomethyl-benzo[b]naphtho[2,3-d]furan To a RB flask was added 7-methyl-benzo[b]naphtho-8 2,3-d]furan (Cambridge Chemicals, Inc., 16.0 g, 0.07 mol), N-bromosuccinimide (Aldrich 12.8 g, 0.072 mol, recrystallized from H₂O and dried under high vacuum overnight), a catalytic amount of benzoyl peroxide (0.01 g) and CCl₄ (1 L). The mixture was refluxed for 2.5 h, cooled and filtered to remove the succinimide formed in the reaction. The solvent was then removed from the reaction mixture by rotary evaporation. The crude product was purified by flush chromatography on SiO₂ using PhCH₃ as the eluting solvent. The appropriate fractions were combined and the solvent once again removed by rotary evaporation to give 22.0 g of product. The material (which was one spot by TLC and pure by NMR) was used without further purification.

6B. 2-[(Benzo[b]naphtho[2,3-d]furan-7-ylmethyl)amino]-2-methyl-1,3-propanediol methanesulfonate.0.25H₂O To a RB flask was added 7-bromomethyl-benzo[b]naphtho[2,3-d]furan (6A, 22.0 g, 0.0706 mol), 2-methyl-2-amino-1,3-propanediol (Aldrich, 14.84 g, 0.141 mol), K₂CO₃ (Mallinckrodt, 19.49 g, 0.141 mol) and abs. ethanol (600 mL). The mixture was refluxed overnight, cooled and filtered. The solvent was then removed by rotary evaporation to give a white residue. This was shaken with hot H₂O (500 mL). The mixture was allowed to stand at RT for 1 h and the resulting solid filtered. The mixture was filtered and the resulting solid washed with warm H₂O (2×500 mL). The damp solid was dissolved in abs. EtOH (400 mL) containing methanesulfonic acid (3 mL). The liquid was filtered through a fine fritted glass funnel and the filtrate diluted to 2 L with Et₂O. The resulting solid was filtered and recrystallized (EtOH/Et₂O, 1:2). After drying in a vacuum oven overnight at 80°, 9.67 g (32% yield) of 2-[(benzo[b]naphtho[2,3-d]furan-7-yl-methyl)amino]-2-methyl-1,3-propanediol methanesulfonate.0.25H₂O, mp 248°-249° (dec), (C, H, N, S).

EXAMPLE 7

2-[(Benzo[b]naphtho[2,3-d]thiophen-6-ylmethyl)amino]-2-methyl-1,3-propanediol

7A. Benzo[b]naphtho[2,3-d]thiophene-6-carbaldehyde

Benzo[b]naphtho[2,3-d]-thiophene (Cambridge Chemicals, Inc.) was formylated using the procedure of A. Rieche et al., *Chem. Ber* 93, 88 (1960), to give a 78.1% yield of benzo[b]naphtho[2,3-d]thiophene-6-carbaldehyde, mp 199°, (C, H, S), (CH₂Cl₂/hexane).

7B. 2-[(Benzo[b]naphtho[2,3-d]thiophen-6-ylmethyl)amino]-2-methyl-1,3-propanediol methanesulfonate Using the procedure outlined in Example 1, benzo[b]naphtho[2,3-d]thiophene-6-carbaldehyde (7A) and 2-amino-2-methyl-1,3-propanediol (Aldrich) gave 67.1% yield of 2-[(benzo[b]naphtho[2,3-d]thiophen-6-ylmethyl)amino]-2-methyl-1,3-propanediol methanesulfonate, mp 242°-243°, (C, H, N, S), (EtOH/Et₂O).

EXAMPLE 8

2-[(Benzo[b]naphtho[2,3-d]thiophen-8-ylmethyl)amino]-2-methyl-1,3-propanediol

8A. Benzo[b]naphtho[2,3-d]thiophene-8-carbaldehyde

To a RB flask equipped with magentic stirring bar, reflux condenser and N₂ inlet line with bubbler was added 2,3-dichloro-5,6-dicyano-1,4-benzoquinone (DDQ) (Aldrich, 38.6 g, 0.119 mol), H₂O (100 mL) and CHCl₃ (1500 mL). After refluxing the mixture for 15 min,. 8-methylbenzo[b]-naphtho-[2,3-d]thiophene (Cambridge Chemicals, Inc., 21.0 g, 89.6 mmol) was added to the flask. After refluxing the mixture for 5 h an additional portion of DDQ (19.3 g, 85 mmol) was added. The mixture was then refluxed overnight, cooled and the deep red solution filtered. The solvent was then removed by rotary evaporation and the residual H₂O removed by azeotropic distillation with several portions of PhCH₃. The material was then dissolved in PhCH₃ (500 mL) and applied to a 40×10 cm column of SiO₂ and eluted with additional PhCH₃ as the solvent. The appropriate fractions were combined and the solvent removed to give 7.12 g of crude material. This was crystallized (PhCH₃), filtered and dried to give 5.35 g (22.7% yield) of benzo[b]naphtho[2,3-d]thiophene-8-carbaldehyde, mp 182°-185°, (C, H, S).

8B. 2-[(Benzo[b]naphtho[2,3-d]thiophen-8-ylmethyl)amino]-2-methyl-1,3-propanediol methanesulfonate.0.6H₂O Using the procedure outlined in Example 1, benzo[b]naphtho[2,3-d]thiophene-8-carbaldehyde (8A) and 2-amino-2-methyl-1,3-propanediol (Aldrich) gave a 60.1% yield of 2-[(benzo[b]naphtho[2,3-d]thiophen-8-ylmethyl)amino]-2-methyl-1,3-propanediol methanesulfonate.0.6H₂O, mp 245°-246° (dec), (C, H, N, S), (EtOH/Et₂O).

EXAMPLE 9

2-[(Benzo[b]naphtho[2,3-d]thiophen-7-ylmethyl)amino]-2-methyl-1,3-propanediol

9A. Benzo[b]naphtho[2,3-d]thiophene-7-carbaldehyde

Using the procedure described in Example 8, 7-methylbenzo[b]-naphtho[2,3-d]thiophene (Cambridge Chemicals, Inc.) gave an 18.7% yield of benzo[b]naphtho[2,3-d]thiophene-7-carbaldehyde, mp 199°-200°, (C, H, S), (PhCH₃/hexane).

9B. 2-[(Benzo[b]naphtho[2,3-d]thiophen-7-ylmethyl)amino]-2-methyl-1,3-propanediol methanesulfonate.0.5H₂O Using the procedure outlined in Example 1, benzo[b]naphtho[2,3-d]thiophene-7-carbaldehyde (9A) and 2-amino-2-methyl-1,3-propanediol (Aldrich) gave a 75.8% yield of 2-[(benzo[b]naphtho[2,3-d]thiophen-7-ylmethyl)amino]-2-methyl-1,3-propanediol methanesulfonate.0.5H₂O, mp 210°-211° (dec), (C, H, N, S), (EtOH/Et₂O).

EXAMPLE 10

2-[(Benzo[b]naphtho[2,3-d]furan-11-ylmethyl)amino]-2-methyl-1,3-propanediol methanesufonate Using the procedure outlined in Example 1, benzo[b]naphtho[2,3-d]-furan-11-carbaldehyde (2B) and 2-amino-2-methyl-1,3-propanediol (Aldrich) gave a 68.8% yield of 2-[(benzo[b]naphtho[2,3-d]furan-11-ylmethyl)amino]-2-methyl-1,3-propanediol methanesulfonate, mp 219°–220° (dec), (C, H, N, S), (EtOH/Et$_2$O).

EXAMPLE 11

2-[(5-Ethyl-5H-benzo[b]carbazol-7-yl)methy]amino]-2-methyl-1,3-propanediol 11A. 5-Ethyl-5H-benzo[b]carbazole-7-carbaldehyde Using the procedure outlined in Example 8A, 5-ethyl-7-methyl-5H-benzo[b]carbazole (Cambridge Chemicals, Inc.) gave a 15.4% 5-ethyl-5H-benzo[b]carbazole-7-carbaldehyde, mp 130°–133°, (C, H, N), (PhCH$_3$).

11B. 2-[(5-Ethyl-5H-benzo[b]carbazol-7-yl)methy]amino]-2-methyl-1,3-propanediol methanesulfonate Using the procedure outlined in Example 1, 5-ethyl-5H-benzo[b]carbazole-7-carbaldehyde (11A) and 2-amino-2-methyl-1,3-propanediol (Aldrich) gave a 40.2% yield of 2-[(5-ethyl-5H-benzo[b]carbazol-7-yl)methy]amino]-2-methyl-1,3-propanediol methanesulfonate, mp 219°–220° (dec), (C, H, N, S), (EtOH/Et$_2$O).

EXAMPLE 12

2-[(5-Ethyl-5H-benzo[b]carbazol-6-yl)methy]amino]-2-methyl-1,3-propanediol 12A.

5-Ethyl-5H-benzo[b]carbazole-6-carbaldehyde

5-Ethyl-6-methyl-5H-benzo[b]carbazole (Cambridge Chemicals, Inc.) was formylated using the procedure of A. Rieche et al., *Chem. Ber.* 93, 88 (1960) to give a 44.9% yield of 5-ethyl-5H-benzo[b]carbazole-6-carbaldehyde, mp 95.5°–96.5°, (C, H, N), (PhCH$_3$).

12B. 2-[(5-Ethyl-5H-benzo[b]carbazol-6-yl)methy]amino]-2-methyl-1,3-propanediol methanesulfonate Using the procedure outlined in Example 1, 5-ethyl-5H-benzo[b]carbazole-6-carbaldehyde (12A) and 2-amino-2-methyl-1,3-propanediol (Aldrich) gave a 68.0% yield of 2-[(5-ethyl-5H-benzo[b]carbazol-6-yl)methyl]amino]-2-methyl-1,3-propanediol methanesulfonate, mp 174°–175°, (C, H, N, S), (EtOH/Et$_2$O).

EXAMPLE 13

2-[(Benzo[b]naphtho[1,2-d]thiophen-5-ylmethyl)amino]-2-methyl-1,3-propanediol

13A. Benzo[b]naphtho[1,2-d]thiophene-5-carbaldehyde

Benzo[b]naphtho[1,2-d]thiophene (H. G. Pars Pharmaceutical Laboratories, Inc.) was formylated using the procedure of A. Rieche et al., *Chem. Ber.* 93, 88 (1960) to give a 49.3% yield of benzo[b]naphtho[1,2-d]thiophene-5-carbaldehyde, mp 142°–144°, (C, H, S), (CH$_2$Cl$_2$/hexane).

13B. 2-[(Benzo[b]naphtho[1,2-d]thiophen-5-ylmethyl)amino]-2-methyl-1,3-propanediol methanesulfonate.0.5H$_2$O Using the procedure outlined in Example 1, benzo[b]naphtho[1,2-d]thiophen-5-carbaldehyde (13A) and 2-amino-2-methyl-1,3-propanediol (Aldrich) gave a 73.7% yield of 2-[(benzo[b]naphtho[1,2-d]thiophen-5-ylmethyl)amino]-2-methyl-1,3-propanediol methanesulfonate.0.5H$_2$O, mp 209°–209.5°, (C, H, N, S), (EtOH/Et$_2$O).

EXAMPLE 14

2-Methyl-2-[(phenanthro[1,2-b]furan-2-ylmethyl)-amino]-1,3-propanediol

14A. Phenanthro[1,2-b]furan-2-methanol

To a RB flask equipped with magentic stirring bar, reflux condenser, N$_2$ inlet tube with bubbler was added ethyl phenanthro(1,2-b]furan-2-carboxylate (H. G. Pars Pharmaceutical Laboratories, Inc., 7.9 g, 27.2 mmol), lithium borohydride (Aldrich, 0.65 g, 30 mmol) and dry THG (400 mL). The mixture was stirred at reflux for 6 h and then poured into H$_2$O (1 L). The reaction mixture was acidified with 1N HCl and the resulting white solid was filtered, washed with additional H$_2$O (1500 mL) then dissolved in CH$_2$Cl$_2$ (500 mL), dried (Na$_2$SO$_4$), filtered, concentrated to 200 mL and diluted to 500 mL with hexane. The resulting material was filtered, washed with hexane (100 mL) and placed in a vacuum oven overnight. A total of 6.1 g (90.1%) of phenanthro[1,2-b]furan-2-methanol, mp 125°–126° was obtained (C, H).

14B. Phenanthro[1,2-b]furan-2-carbaldehyde

To a RB flask equipped with magnetic stirring bar, reflux condenser, N$_2$ inlet line with bubbler was added phenanthro[1,2-b]furan-2-methanol (14A, 5.84 g, 23.5 mmol), barium manganate (Aldrich, 12.06 g, 47 mmol) and dry CH$_2$Cl$_2$ (400 mL). The mixture was refluxed for 6 h, filtered and the resulting dark yellow solution filtered through a small plus of SiO$_2$ to remove inorganic salts and polar baseline material. The solvent was then removed by rotary evaporation and the crude material recrystallized using CH$_2$Cl$_2$/hexane to give after drying 5.17 g (91% yield) of phenanthro[1,2-d]furan-2-carbaldehyde, mp 169°, (C, H).

14C. 2-Methyl-2-[(phenanthro[1,2-b]furan-2-ylmethyl)amino]-1,3-propanediol methanesulfonate.0.5H$_2$O Using the procedure outlined in Example 1, phenanthro[1,2-b]furan-2-carbaldehyde (14B) and 2-amino-2-methyl-1,3-propanediol (Aldrich) gave a 57.1% yield of 2-methyl-2-[(phenanthro[1,2-b]furan-2-ylmethyl)amino]-1,3-propanediol methanesulfonate.0.5H$_2$O, mp 168°–170° (dec), (C, H, N, S), (EtOH/Et$_2$O).

EXAMPLE 15

2-Methyl-2-[(phenanthro[1,2-b]furan-11-ylmethyl)amino]-1,3-propanediol

15A. Ethyl 11-formyl-phenanthro[1,2-b]furan-2-carboxylate

Ethyl phenanthro[1,2-b]furan-2-carboxylate (H. G. Pars Pharmaceutical Laboratories, Inc.) was formylated by the procedure of A. Rieche et al., *Chem. Ber.* 93, 88 (1960) to give a crude mixture of aldehydes in 54% yield which was used in the next step without purification. An analytical sample of the main component of this mixture, ethyl 11-formylphenanthro-[1,2-b]furan-2-carboxylate, mp 209°–212° was produced by column chromatography followed by crystallization, (C,H), (CH$_2$Cl$_2$/hexane).

15B. Phenanthrol[1,2-B]furan-11-carbaldehyde

To a RB flask equipped with a magnetic stirring bar, condenser, and N$_2$ inlet line with bubbler was added ethyl 11-formyl-phenanthro[1,2-b]furan-2-carboxylate (15A, 2.5 g, 7.8 mmol), 1NaOH solution (25 mL), THF (50 mL) and H$_2$O (25 mL). The mixture was refluxed for 2 h until it became homogeneous. The mixture was acidified with 1N HCl and the solvent removed by rotary evaporaton. The crude solid was then heated to 150° with copper powder (0.9 g) and quinoline and (Aldrich, 25 mL) for 1 h. The reaction mixture was cooled and the quinoline removed under vacuum to give a crude dark green solid. After chromatography and cyrstallization ($CH_2Cl_2$/hexane) 0.71 g (37% yield) of phenanthro[1,2-b]furan-11-carbaldehyde, mp 145°–150°, (C,H).

15C. 2-Methyl-2-[(phenanthro[1,2-b]furan-11-ylmethyl)amino]-1,3-propanediol methanesulfonate Using the procedure outlined in Example 1, phenanthro[1,2-b]furan-11-carbaldehyde (15B) and 2-amino-2-methyl-1,3-propanediol (Aldrich) gave a 57.6% yield of 2-methyl-2-[(phenanthro[1,2-b]furan-11-ylmethyl)amino]-1,3-propanediol methanesulfonate, mp 186°–188° (dec), (C,H,N,S), (EtOH/$Et_2O$).

EXAMPLE 46

2-Methyl-2-[(phenanthro[1,2-b]thiophen-2-ylmethyl)amino]-1,3-propanediol

16A. Phenanthro[1,2-b]thiophene-2-methanol

Using the procedure outlined in 14A, ethyl phenanthro[1,2-b]thiophene-2-carboxylate (H. G. Pars Pharmaceutical Laboratories, Inc.) gave a 98.0% yield of phenanthro[1,2-b]thiophene-2-methanol, mp 169°–170.5° (C,H,S), ($CH_2Cl_2$/hexane).

16B. Phenanthro[1,2-b]thiophene-2-carbaldehyde

Using the procedure outlined in 14B, phenanthro[1,2-b]thiophene-2-methanol (16A) gave a 82.9% yield of phenanthro[1,2-b]thiophene-2-carbaldehyde, mp 209°–210°, (C,H,S), ($CH_2Cl_2$/hexane).

16C. 2-Methyl-2-[(phenanthro[1,2-b]thiophen-2-ylmethyl)amino]-1,3-propanediol methanesulfonate.0.6 $H_2O$ Using the procedure outlined in Example 1, phenanthro[1,2-b]-thiophene-2-carbaldehyde (16B) and 2-amino-2-methyl-1,3-propanediol (Aldrich) gave an 82.7% yield of 2-methyl-2-[(phenanthro[1,2-b]-thiophene-2-ylmethyl)amino]-1,3-propanediol methanesulfonate.0.6 $H_2O$, mp 209°–209.5° (dec), (C,H,N,S), ($CH_3OH$/$Et_2O$).

EXAMPLE 17

2-Methyl-2-[(phenathro[1,2-b]thiophen-11-ylmethyl)amino]-1,3-propanediol

17A. Phenanthro[1,2-b]thiophene-11-carbaldehyde

Ethyl phenanthro[1,2-b]thiophene-2-carboxylate was formylated using the procedure of A. Rieche et al., Chem. Ber. 93, 88 (1960), to give a low yield of a mixture of aldehyde esters. The mixture of aldehyde esters. The mixture was directly hydrolyzed as in Example 15B and the resulting crude mixture of aldehyde acids was decarboxylated as in Example 15B to give a crude mixture of aldehydes. The main component of the mixture, phenanthro[1,2-b]thiophene-11-carbaldehyde, mp 161.5°–162.5° was obtained after chromatography and crystallization in 3.1% overall yield, (C,H,S), ($PhCH_3$).

17B. 2-Methyl-2-[(phenanthro[1,2-b]thiophene-11-ylmethyl)amino]-1,3-propanediol methanesulfonate Using the procedure outlined in Example 1, phenanthro[1,2-b]thiophene-11-carbaldehyde (17A) and 2-amino-2-methyl-1,3-propanediol (Aldrich) gave a 56.5% yield of 2-methyl-2-[(phenanthro[1,2-b]thiophen-11-ylmethyl)amino]-1,3-propanediol methanesulfonate, mp 206°–207° (dec), (C,H,N,S), (EtOH/$Et_2O$).

EXAMPLE 18

2-Methyl-2-[(phenanthro[4,3-b]furan-2-ylmethyl)amino]-1,3-propanediol

18A. Phenanthro[4,3-b]furan-2-methanol

Using the procedure outlined in Example 14A, ethyl phenanthro[4,3-b]furan-2-carboxylate (H. G. Pars. Pharmaceutical Laboratories, Inc.) gave a 91% yield of phenanthro[4,3-b]furan-2-methanol, mp 125°–126°, (C,H), ($CH_2Cl_2$/hexane).

18B. Phenanthro[4,3-b]furan-2-carbaldehyde

Using the procedure outlined in Example 14B, phenanthro[4,3-b]furan-2-methanol (18A) gave a 91.2% yield of phenanthro[4,3-b]furan-2-carbaldehyde, mp 169°, (C,H), (95% EtOH/$CH_2Cl_2$).

18C. 2-Methyl-2-[(phenanthro[4,3-b]furan-2-ylmethyl)amino]-1,3-propanediol methansulfonate Using the procedure outlined in Eample 1, phenanthro[4,3-b]furan-2-carbaldehyde (18B) and 2-amino-2-methyl-1,3-propanediol (Aldrich) gave a 56.5% yield of 2-methyl-2-[(phenanthro[4,3-b]furan-2-yl)methyl)amino]-1,3-propanediol methanesulfonate, mp 186°–188° (dec), (C,H,N,S), (EtOH/$Et_2O$).

EXAMPLE 19

2-Methyl-2-[(phenanthro[4,3-b]thiophene-7-ylmethyl)amino]-1,3-propanediol

19A. Phenanthro[4,3-b]thiophene-7-carbaldehyde

Using the procedure outlined in Example 17A ethyl phenanthro[4,3-b]thiophene-2-carboxylate (H. G. Pars Pharmaceutical Laboratories, Inc.) gave a 6.7% yield of phenanthro[4,3-b]thiophene-7-carbaldehyde, mp 173°–177° (C,H,S), ($PhCH_3$).

19B. 2-Methyl-2-[(phenanthro[4,3-b]thiophen-7-ylmethyl)amino]-1,3-propanediol methanesulfonate.0.25 $H_2O$ Using the procedure outlined in Example 1, phenanthro[4,3-b]thiophene-7-carbaldehyde (19A) and 2-amino-2-methyl-1,3-propanediol (Aldrich) gave a 53.8% yield of 2-methyl-2-[(phenanthro[4,3-b]-thiophen-7-ylmethyl)amino]-1,3-propanediol methanesulfonate.0.25 $H_2O$, mp 189°–191° (dec), (C,H,N,S), (EtOH/$Et_2O$).

EXAMPLE 20

2-Methyl-2-[(phenanthro[9,10-b]furan-2-ylmethyl)amino]-1,3-propanediol

20A. Phenanthro[9,10-b]furan-2-carbaldehyde

Phenanthro[9,10b]furan (prepared by the procedure of P. Muller and J. Pfyffer, Chimia 38, 79 (1984)) was formylated using the procedure of A. Rieche et al., ;I Chem. Ber. 93, 88 (1960) to give a 32.8% yield of phenanthro[9,10-b]furan-2-carbaldehyde, mp 84°–85°, (C,H), ($PhCH_3$).

20B. 2-Methyl-2-[(phenanthro[9,10-b]furan-2-ylmethyl)amino]-1,3-propanediol methanesulfonate.0.2 $H_2O$.0.2 EtOH Using the procedure outlined in Example 1, phenanthro[9,10-b]furan-2-carbaldehyde (20A) and 2-amino-2-methyl-1,3-propanediol (Aldrich) gave a 39.2% yield of 2-methyl-2-[(phenanthro[9,10-b]furan-2-ylmethyl)amino]-1,3-propanediol methanesulfonate.0.2 $H_2O$.0.2 EtOH, mp 218°–219°(dec), (C,H,N,S), (EtOH/$Et_2O$).

EXAMLE 21

2-Methyl-2-[(phenanthro[9,10-c]thiophen-1-ylmethyl)amino]-1,3-propanediol

21A. Phenanthro[9,10-c]thiophene-1-carbaldehyde

Phenanthro[9,10-c]thiphene (H. G. Pars Pharmaceutical Laboratories, Inc.) was formylated using the procedure of A. Rieche et al., *Chem. Ber.* 93, 88 (1960) to give a 85.9% yield of phenanthro[9,10-c]thiophene-1-carbaldehyde, mp 198°–199°, (C,H,S), (THF/95% EtOH).

21B. 2-Methyl-2-[(phenanthro[9,10-c]thiophen-1-ylmethyl)amino]-1,3-propanediol methanesulfonate.0.25 $H_2O$ Using the procedure outlined in Example 1, phenanthro[9,10-c]-thiophene-1-carbaldehyde (21A) and 2-amino-2-methyl-1,3-propanediol (Aldrich) gave a 39.2% yield of 2-methyl-2-[(phenanthro[9,10-c]thiophen-1-ylmethyl)amino]-1,3-propanediol methanesulfonate.0.25 $H_2O$, mp 180°–187° (dec), (C,H,N,S), (EtOH/$Et_2O$).

EXAMPLE 22

2-[Acenaphtho-[1,2-b]-thiophen-8-ylmethyl)amino]-2-methyl-1,3-propanediol hydrochloride Using the procedure outlined in Example 1, acenaphtho[1,2-b]thiophene-8-carbaldehyde (H. G. Pars Pharmaceutical Laboratories, Inc.) and 2-amino-2-methyl-1,3-propanediol (Aldrich) gave a 73.8% yield of 2-[8-acenaphtho-[1,2-b]thiophen-8-ylmethyl)amino]-2-methyl-1,3-propanediol hydrochloride, mp 208°–210° (dec), (C,H,N,Cl,S), (EtOH/$Et_2O$).

EXAMPLE 23

2-[Acenaphtho-[1,2-c]-thiophen-7-ylmethyl)amino]-2-methyl-1,3-propanediol

23A. Acenaphtho[1,2-c]-thiophene-7-carbaldehyde

Acenaphtho[1,2-c]thiophene (H. G. Pars Pharmaceutical Laboratories, Inc.) was formylated according to the procedure of A. Rieche et al., *Chem. Ber.* 93, 88 (1960) to give an 83.2% yield of acenaphtho[1,2-c]thiophene-7-carbaldehyde, mp 123°–125.5°, (C,H,S).

23B. 2-[Acenaphtho-[1,2-c]thiophen-7-ylmethyl)amino]-2-methyl-1,3-propanediol hydrochloride Using the procedure outlined in Example 1, acenaphtho[1,2-c]-thiophene-7-carbaldehyde (23A) and 2-amino-2-methyl-1,3-propanediol (Aldrich) gave a 57.4% yield of 2-[(acenaphtho-[1,2-c]thiophen-7-ylmethyl)amino]-2-methyl-1,3-propanediol hydrochloride, mp 220°–223° (dec), (C,H,N,Cl,S), (EtOH/$Et_2O$).

Antitumor Screening Results

Methods for evaluating the antitumor activity of these compounds are essentially those used in the Tumor Panel by the Developmental Therapeutics Program, Division of Cancer Treatment, National Cancer Institute, A. Goldin, et al., *Methods in Cancer Research*, Vol. XVI, p. 165, Academic Press (1979). Some modifications, in dose level and schedule have been made to increase the testing efficiency.

EXAMPLE 24

Lymphocytic Leukemia P388/0 Test $CD2-F_1$ mice, of the same sex, weighing 20±3 g, are used for this test. Control and test animals are injected intraperitoneally with a suspension of ~$10^6$ viable P388/0 tumor cells on day 0. In each test, several dose levels which bracket the $LD_{20}$ of the compound are evaluated; each dose level group contains six animals. The test compounds are prepared either in physiologic saline containing 0.05% Tween 80 or distilled water containing 5% dextrose and are administered intraperitoneally on days 1, 5, and 9 relative to tumor implant. Doses are on a mg/kg basis according to individual animal's body weights. The day of death for each animal is recorded, the median identified for each group and the ratios of median survival time for treated (T)/control (C) groups are calculated. The criterion for activity is T/C×100≧120%. Results of P388/0 testing are summarized in Table I.

TABLE I

| Compound of Formula | Optimal Dose (mg/kg) | T/C × 100% (Excluding 30 Day Survivors) | 30 Day Survivors | $LD_{20}$ (mg/kg) |
| --- | --- | --- | --- | --- |
| 1 | 65 | +225 | 0/6 | 35 |
| 2B | 100 | +250 | 1/6 | 50 |
| 3B | 20 | +230 | 2/6 | 10 |
| 4D | 80 | >+300 | 6/6 | 55 |
| 5B | 125 | +255 | 4/6 | 100 |
| 6B | 65 | +210 | 0/6 | 35 |
| 7B | 450 | +158 | 0/6 | 400 |
| 9B | 110 | +205 | 0/6 | 140 |
| 10 | 400 | +290 | 2/5 | 320 |
| 12B | 175 | +140 | 0/6 | 200 |
| 13B | 20 | +155 | 0/6 | 20 |
| 15C | 120 | +227 | 1/6 | 120 |
| 17B | 120 | +223 | 0/6 | 120 |
| 19B | 2.5 | +145 | 0/6 | 1.0 |
| 20B | 175 | +167 | 0/6 | 175 |
| 21B | 320 | +140 | 0/6 | 320 |
| 23B | 350 | +120 | 0/6 | 300 |

EXAMPLE 25

Formulation Examples

| A. TABLET | |
| --- | --- |
| Compound of Formula I | 500.0 mg |
| Pregelatinized Corn Starch | 60.0 mg |
| Sodium Starch Glycolate | 36.0 mg |
| Magnesium Stearate | 4.0 mg |

The compound of formula (I) is finely ground and intimately mixed with the powdered excipients, pregelatinized corn starch and sodium starch glycolate. The powders are wetted with purified water to form granules. The granules are dried and mixed with the magnesium stearate. The formulation is then compressed into tablets weighing approximately 600 mg each.

| B. TABLET | |
| --- | --- |
| Compound of formula (I) | 500.0 mg |
| Corn Starch | 70.0 mg |
| Lactose | 83.8 mg |
| Magnesium Stearate | 4.2 mg |
| Polyvinylpyrrolidone | 14.0 mg |
| Stearic Acid | 28.0 mg |

The compound of formula (I) is finely ground and intimately mixed with the powdered excipients, corn starch and lactose. The powders are wetted with a solution of polyvinylpyrrolidone dissolved in a mixture of purified water and denatured alcohol to form granules. The granules are dried and mixed with the powdered stearic acid and magnesium stearate. The formulation is then compressed into tablets weighing approximately 700 mg each.

| C. CAPSULES | |
|---|---|
| Compound of formula (I) | 500.0 mg |
| Corn Starch | 50.0 mg |
| Magnesium Stearate | 3.0 mg |

The finely divided compound of formula (I) is mixed with powdered corn starch and wetted with denatured alcohol to densify the powder. The dried powder is mixed with stearic acid and filled into hard-shell gelatin capsules.

| D. SYRUP | |
|---|---|
| Compound of formula (I) | 250.0 mg |
| Ethanol | 250.0 mg |
| Glycerin | 500.0 mg |
| Sucrose | 3,500.0 mg |
| Flavoring Agent | q.s. |
| Coloring Agent | q.s. |
| Preserving Agent | 0.1% |
| Purified Water q.s. to | 5.0 mL |

The compound of formula (I) is dissolved in the ethanol, glycerin, and a portion of the purified water. The sucrose and preserving agent are dissolved in another portion of hot purified water, and then the coloring agent is added and dissolved. The two solutions are mixed and cooled before the flavoring agent is added. Purified water is added to final volume. The resulting syrup is throughly mixed.

| E. IV INJECTION | |
|---|---|
| Compound of formula (I) | 5.0 mg |
| Glycerin | q.s. for isotonicity |
| Preservative | 0.1% |
| Hydrochloric Acid or Sodium Hydroxide | as needed for pH adjustment |
| Water for Injection | q.s. to 1 mL |

The compound of formula (I) and preservative is added to the glycerin and a portion of the water for injection. The pH is adjusted with hydrochloric acid or sodium hydroxide. Water for injection is added to final volume and solution is complete after thorough mixing. The solution is sterilized by filtration through a 0.22 micrometer membrane filter and aseptically filled in sterile 10 mL ampules or vials.

What is claimed is:

1. A compound of formula (I)

$$ArCH_2R^1 \quad (I)$$

an acid addition salt thereof or a $C_{1-6}$ alkylcarboxylic acid ester derived therefrom;

the Ar ring system is unsubstituted, mono-substituted or di-substituted, the substituents contain not more than four carbon atoms in total when taken together being the same or different and are selected from halogen; cyano; $C_{1-4}$ alkyl or $C_{1-4}$ alkoxy, each optionally substituted by hydroxy or $C_{1-2}$ alkoxy; halogen substituted $C_{1-2}$ alkyl or $C_{1-2}$ alkoxy; a group $S(O)_nR^2$ wherein n is an integer 0, 1 or 2 and $R^2$ is $C_{1-2}$ alkyl optionally substituted by hydroxy or $C_{1-2}$ alkoxy; or the Ar ring is optionally substituted by a group $NR^3R^4$ containing not more than 5 carbon atoms wherein $R^3$ and $R^4$ are the same or different and each is a $C_{1-3}$ alkyl group; and Ar is

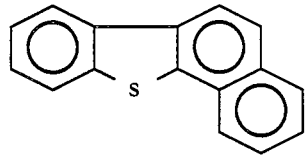

or

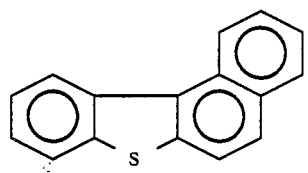

$R^1$ contains not more than eight carbon atoms and is a group

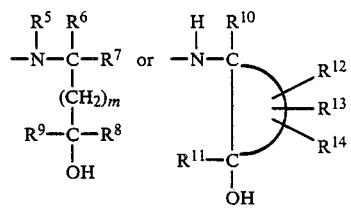

wherein
m is 0 or 1;
$R^5$ is hydrogen;
$R^6$ and $R^7$ are the same or different and each is hydrogen or $C_{1-5}$ alkyl optionally substituted by hydroxy;
$R^8$ and $R^9$ are the same or different and each is hydrogen or $C_{1-3}$ alkyl;

is a five- or six-membered saturated carboxyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl.

2. The compound of claim 1 wherein $R^1$ is

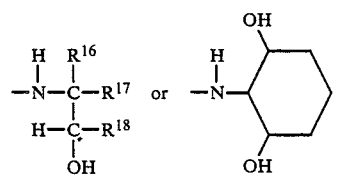

wherein m is 0; $R^{16}$ is $CH_2OH$, $CH(CH_3)OH$ or $CH_2CH_2OH$; $R^{17}$ is hydrogen, $C_{1-3}$ alkyl or $CH_2OH$; $R^{18}$ is hydrogen or methyl.

3. A compound of claim 1 wherein $R^1$ is a diol of the structure

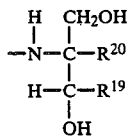

wherein $R^{19}$ is hydrogen or methyl and $R^{20}$ is hydrogen, methyl or ethyl.

4. A compound of claim 3 wherein $R^{20}$ is methyl.

5. A compound of claim 1 which is 2-[(benzo[b]naphtho[1,2-d]-thiophen-5-ylmethyl)amino]-2-methyl-1,3-propanediol or a $C_{1-6}$ alkylcarboxylic acid ester derived therefrom or a pharmaceutically acceptable acid addition salt thereof.

6. 2-[(Benzo[b]naphtho[1,2-d]thiophen-5-ylmethyl)amino]-2-methyl-1,3-propanediol methansulfonate.

7. 2-[(Benzo[b]naphtho[2,1-d]thiophen-5-ylmethyl)amino]-2-methyl-1,3-propanediol or a pharmaceutically acceptable acid addition salt thereof.

* * * * *